United States Patent [19]
Scholl et al.

[11] Patent Number: 5,786,438
[45] Date of Patent: Jul. 28, 1998

[54] MIXTURES OF CYCLOALIPHATIC DIISOCYANATES, A PROCESS FOR THEIR PREPARATION AND THEIR USE FOR THE PRODUCTION OF POLYISOCYANATE ADDITION PRODUCTS

[75] Inventors: Hans-Joachim Scholl; Bernhard Jansen, both of Köln; Klaus Jost, Dormagen; Rolf-Volker Meyer, Leverkusen, all of Germany

[73] Assignee: Bayer Aktiengesellschaft, Leverkusen, Germany

[21] Appl. No.: 831,448

[22] Filed: Mar. 31, 1997

[30] Foreign Application Priority Data

Apr. 11, 1996 [DE] Germany ............... 196 14 270.9

[51] Int. Cl.$^6$ .................................................. C08G 18/75
[52] U.S. Cl. ................... 528/67; 528/85; 560/330; 560/347
[58] Field of Search ............ 528/67, 85; 560/347, 560/330

[56] References Cited

U.S. PATENT DOCUMENTS 4,394,495 7/1983 Scholl ............................ 528/67

FOREIGN PATENT DOCUMENTS

| 1207340 | 7/1986 | Canada . |
| 1239415 | 7/1988 | Canada ............... 260/456.4 |
| 1248552 | 1/1989 | Canada ............... 260/605.8 |
| 3317875 | 11/1984 | Germany . |

Primary Examiner—Rachel Gorr
Attorney, Agent, or Firm—Joseph C. Gil; Thomas W. Roy

[57] ABSTRACT

The present invention relates to mixtures of cycloaliphatic diisocyanates corresponding to formula 1)

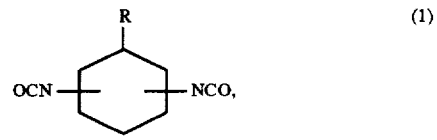

wherein

R represents a saturated, linear, aliphatic hydrocarbon residue having 8 to 15 carbon atoms.

The present invention also relates to a process for the preparation of these diisocyanate mixtures and to their use for the production of polyisocyanate addition products.

3 Claims, No Drawings

MIXTURES OF CYCLOALIPHATIC DIISOCYANATES, A PROCESS FOR THEIR PREPARATION AND THEIR USE FOR THE PRODUCTION OF POLYISOCYANATE ADDITION PRODUCTS

BACKGROUND OF THE INVENTION

1. Field of the Invention

The present invention relates to homolog and isomer mixtures of cycloaliphatic diisocyanates, a process for the preparation of these diisocyanates and their use for the production of polyisocyanate addition products.

2. Description of the Prior Art

Cycloaliphatic diisocyanates are known and are conventionally prepared by ring hydrogenation of the corresponding aromatic diamines and subsequent phosgenation of the resulting cycloaliphatic diamines. For example, methylcyclohexanediamine isomer mixtures may be produced by ring hydrogenation from diaminotoluene and then phosgenated to yield the corresponding methylcyclohexane diisocyanate isomer mixture. Disadvantages of this known process at the hydrogenation stage are a) deamination reactions caused by the severe hydrogenation conditions, which reduce yield and result in unwanted monoisocyanates after phosgenation, and b) the increased percentage of cis diamino isomers, which, due to their immediately adjacent position, can enter into an undesirably large number of intramolecular secondary reactions. Thus, during conventional phosgenation processes, they form intramolecular urea linkages, which then biuretize resulting in dramatic reductions in isocyanate yields.

An object of the present invention is to provide cyclohexane diisocyanate derivatives which are obtainable using a simple process and which do not suffer from the previously described disadvantages to the same degree as prior art derivatives.

This object may be achieved by the process according to the invention described below.

SUMMARY OF THE INVENTION

The present invention relates to mixtures of cycloaliphatic diisocyanates corresponding to formula 1)

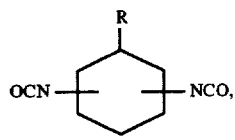

(1)

wherein

R represents a saturated, linear, aliphatic hydrocarbon residue having 8 to 15 carbon atoms.

The present invention also relates to a process for the preparation of these diisocyanate mixtures by ring hydrogenating compounds corresponding to formula 2)

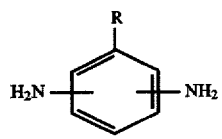

(2)

to provide compounds corresponding to formula 3)

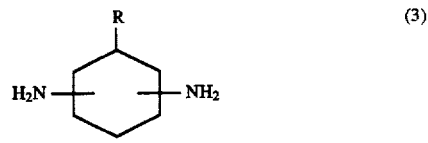

(3)

wherein R has the same meaning set forth above, and subsequently phosgenating the amino groups of the compounds corresponding to formula 3) to obtain the mixtures of cycloaliphatic diisocyanates corresponding to formula 1).

Finally, the present invention relates to the use of the diisocyanate mixtures for the production of polyisocyanate addition products.

DETAILED DESCRIPTION OF THE INVENTION

Starting materials for the process according to the invention are diamines 3), which may be produced according to EP 0 058 335; Canadian Patent 1,207,340; or U.S. Pat. No. 4,394,495, herein incorporated by reference. Due to the long, linear alkyl chains, the n-$C_8$-$C_{15}$-alkylcyclohexane diisocyanates according to the invention are obtained in a simple manner by ring hydrogenation and subsequent phosgenation without appreciable quantities of "monoisocyanate" secondary products and with a comparatively reduced proportion of "biuret" secondary products, which consume isocyanate groups and originate from cis diamino isomers. This finding, which is essential to the invention, is extraordinarily surprising.

The first stage of the process according to the invention involves a known ring hydrogenation, i.e., a catalytically initiated hydrogenation of the aromatic ring. The catalysts used are conventional compounds suitable for ring hydrogenation.

The diamines of formula 3) resulting from this ring hydrogenation correspond to the statements made with regard to the position of the amino groups for starting material 2).

To produce the diisocyanate mixtures according to the invention, diamines 3) are subjected to a known phosgenation reaction, e.g., by dissolving the diamine in a co-solvent such as chlorobenzene and adding it dropwise to a solution of phosgene in chlorobenzene with stirring and cooling at −10° to 0° C. (low temperature phosgenation). The reaction mixture is slowly heated to reflux with continued stirring and introduction of phosgene to convert the initially formed carbamic acid chloride into the desired diisocyanate (high temperature phosgenation). The reaction mixture is then worked up in a known manner. The diamines may also be converted into the diisocyanates according to the invention using any other desired known phosgenation methods, for example, using solvent-free phosgenation processes or by gas phase phosgenation of the diamines.

The diisocyanates according to the invention are liquid substances at room temperature, which are substantially free of monoisocyanates. Any quantities of biuret that may be present as a result of the process may readily be removed by distillation. Undistilled products, but preferably distillates, are valuable chain extenders for the production of polyisocyanate addition products by reaction with compounds containing at least two isocyanate-reactive groups, preferably hydroxyl groups.

EXAMPLES

Example A (Production of an amine starting compound)

An aromatic diamine in the form of a homolog and isomer mixture according to EP 0,058,335, having an alkyl chain length of 10 to 13 C atoms and a mean chain length of approximately 12 C atoms was used in this example.

776 g of diamine, 763 g of tert.-butanol and 7.7 g of ruthenium oxide hydrate were introduced into a 3 liter stirred autoclave. The autoclave was purged three times with nitrogen and pressurized to 138 bar with hydrogen. The contents heated to 180° C. with stirring and the aromatic diamine was ring hydrogenated at a pressure range of 270 to 259 bar. After a reaction time of 5 hours, hydrogen absorption ceased. Once the autoclave was depressurized and the catalyst was separated, the filtrate was concentrated in a rotary evaporator and the crude amine was then distilled under reduced pressure. 739 g of a diamine mixture was obtained as a fraction boiling at 130° to 152° C./0.1 mbar (yield: 95%).

Example 1

(Production of a diisocyanate according to the invention)

The diamine according to Example A in the form of a homolog and isomer mixture having an alkyl chain length of 10 to 13 C atoms and a mean chain length of approximately 12 C atoms was used in this example.

2 liters of dry chlorobenzene were introduced into a 4 liter four-necked flask equipped with stirrer, thermometer, gas inlet line and reflux condenser. 500 g of phosgene were condensed into the flask with stirring and cooling (−10° C). 370 g of diamine, dissolved in 300 g of chlorobenzene, were then added dropwise with cooling to −10° to −5° C. The temperature was slowly increased to reflux temperature, while still introducing phosgene. After the evolution of hydrogen chloride had ceased, excess phosgene was removed with a stream of nitrogen and the solution was evaporated under a vacuum. 345 g of crude isocyanate mixture having an NCO content of 19.1% (theoretical: 25.1%) was obtained, which, according to IR spectroscopy, contained small amounts of biuret.

The resulting crude product was suitable without further purification as a starting material for the production of polyurethanes. The crude product was also subjected to purification by distillation. 300 g of the crude product were distilled under a reduced pressure of 0.5 mbar and within the temperature range of 150° to 175° C., 225 g of a virtually colorless mixture of diisocyanates were obtained, which corresponded to formula 4

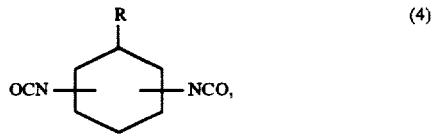

(4)

wherein R has the meaning set forth above.

| Analysis (%) | NCO | C | H | N |
|---|---|---|---|---|
| actual: | 25.0 | 71.7 | 10.4 | 8.2 |
| theoretical: (relative to $C_{20}H_{34}N_2O_2$) | 25.1 | 71.9 | 10.2 | 8.4 |

According to nuclear magnetic resonance measurements, the isocyanate groups of the diisocyanate were in trans arrangement in meta position relative to each other.

Application Examples

Example 2

(Production of water dispersible polyisocyanates for use as sizing agents)

85 g of the distilled isocyanate from Example 1 were introduced into a vessel at 60° C. and 15 g of a polyether started on ethylene glycol monomethyl ether and having an average molecular weight of 350 g/mol were stirred in. Stirring was continued until the isocyanate content was 20.4%.

The resulting product was a storage-stable, water-white liquid which was readily dispersible in water.

Example 3

(Sizing of paper)

Paper having a weight of 80 g/m² was treated with the aqueous polyisocyanate dispersion from Example 2 in a model HF laboratory sizing press supplied by Mathis, Zürich, Switzerland. In addition to the sizing agents described in Table 2, the liquors also contained 5% starch (Perfectamyl from AVEBE, Netherlands). The papers finished in this manner were dewatered by pressing with felt and then dried for 10 minutes at 90° C. in a drying cabinet.

Sizing action was determined by the Cobb test. In this test single-sided water absorption of a paper within 60 seconds was determined gravimetrically. The value found was an indication of the degree of sizing; the values were shown in the following Table.

| Sizing agent | Quantity used (% active substance) | Cobb value |
|---|---|---|
| Aquapel 2B* | 0.15 | 22.4 |
| Baysynthol KSN-W** | 0.15 | 27.9 |
| Product from Example 2 | 0.15 | 21.4 |

*Product of Hercules, contains approx. 12% active substance (Comparison)
**Product of Bayer AG, contains approx. 21.4% active substance (Comparison)

Example 4

(Production of a polyurethane-urea soluble in alcohol/mineral spirits)

70 g of a polyesterdiol based on adipic acid/1,6-hexanediol/neo-pentyl glycol (1:0.71:0.45 molar ratio, OH number 66) and 24.7 g of a polyesterdiol based on phthalic anhydride/ethylene glycol (OH number 281) were dehydrated, mixed with 100 g of the diisocyanate from Example 1 and reacted for two hours at 100° to 105° C. to yield a semi-prepolymer having an NCO content of 8.3%. The prepolymer was diluted with 337 g of mineral spirits (boiling point 155 to 185), cooled to approximately 15° C. and 208 g of isopropanol were added. A solution prepared from 54.3 g of diamine of Example A, 167 g of isopropanol and 40 g of 2-methoxypropanol was then added dropwise at 15° to 25° C. to the clear solution in such a manner that amine chain extension proceeded rapidly. Dropwise addition was terminated just before the equivalence point (IR monitoring: solution exhibited only a minimal NCO band). 98% of the solution to be added dropwise had then been consumed. A mobile, clear solution having a solids content of 25% and a viscosity (25° C.) of 33 mPa•s was obtained. A product produced in the same manner having a solids content of 50% was also a clear solution and had a viscosity (25° C.) of 17,000 mPa•s.

Example 5

(Comparative Example)

When Example 4 was repeated to produce a solution having a solids content of 25% with the exception that the diisocyanate and diamine were replaced with equimolar quantities of isophorone diisocyanate and isophoronediamine, respectively, i.e., other cycloaliphatic compounds, clear solutions were not obtained at any phase of the production process. The turbid liquid became increasingly non-homogeneous as chain extension proceeded, such that chain extension was terminated due to the formation of a two-phase system after the addition of 80% of the amine solution.

Examples 4 and 5 demonstrate that clear solutions with mineral spirits may only be obtained using the diisocyanate according to the invention. This constitutes a technical advantage, because it has previously been necessary to use toxicologically questionable solvents, such as toluene or dimethylformamide, instead of mineral spirits to obtain usable, clear solutions.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A mixture of cycloaliphatic diisocyanates corresponding to formula (1)

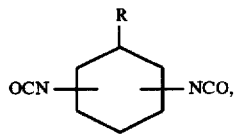

(1)

wherein

R represents a saturated, linear, aliphatic hydrocarbon residue having 8 to 15 carbon atoms.

2. A process for the preparation of the diisocyanate mixtures of claim 1 which comprises ring hydrogenating compounds corresponding to formula 2)

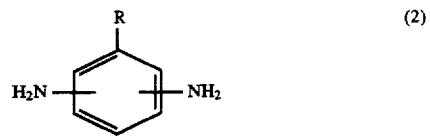

(2)

to form compounds corresponding to formula 3)

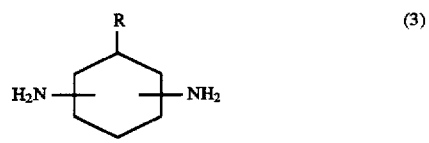

(3)

wherein

R represents a saturated, linear, aliphatic hydrocarbon residue having 8 to 15 carbon atoms, and subsequently phosgenating the amino groups of the compound corresponding to formula 3) to obtain the mixture of cycloaliphatic diisocyanates corresponding to formula 1).

3. A polyisocyanate addition product prepared from the mixture of cycloaliphatic diisocyanates of claim 1 and a compound containing at least two isocyanate-reactive groups.

* * * * *